US012723065B2

(12) United States Patent
Lee et al.

(10) Patent No.: US 12,723,065 B2
(45) Date of Patent: Sep. 1, 2026

(54) METHOD FOR ISOLATING AND CULTURING CORD BLOOD STEM CELLS EXPRESSING GDF-3 AT HIGH LEVEL, AND USE OF GDF-3

(71) Applicant: PRIMORIS THERAPEUTICS Co., Ltd., Gwangmyeong-si (KR)

(72) Inventors: Jae-yong Lee, Gwangju-si (KR); Hee-jin Ahn, Seoul (KR); Yea-in Lee, Gwangmyeong-si (KR); Dong-yeol Lee, Seoul (KR); Kyu-heum Na, Suwon-si (KR)

(73) Assignee: PRIMORIS THERAPEUTICS Co., Ltd., Gwangmyeong-si (KR)

( * ) Notice: Subject to any disclaimer, the term of this patent is extended or adjusted under 35 U.S.C. 154(b) by 567 days.

(21) Appl. No.: 18/265,142

(22) PCT Filed: Dec. 6, 2021

(86) PCT No.: PCT/KR2021/018355
§ 371 (c)(1),
(2) Date: Jun. 2, 2023

(87) PCT Pub. No.: WO2022/119418
PCT Pub. Date: Jun. 9, 2022

(65) Prior Publication Data

US 2023/0406897 A1 Dec. 21, 2023

(30) Foreign Application Priority Data

Dec. 4, 2020 (KR) ........................ 10-2020-0168691

(51) Int. Cl.

| | |
|---|---|
| ***C07K 14/475*** | (2006.01) |
| ***A61K 8/64*** | (2006.01) |
| ***A61K 38/18*** | (2006.01) |
| ***A61P 17/00*** | (2006.01) |
| ***A61Q 19/00*** | (2006.01) |
| ***C12N 5/0775*** | (2010.01) |

(52) U.S. Cl.
CPC .............. *C07K 14/475* (2013.01); *A61K 8/64* (2013.01); *A61K 38/18* (2013.01); *A61P 17/00* (2018.01); *A61Q 19/00* (2013.01); *C12N 5/0665* (2013.01)

(58) Field of Classification Search
CPC ........ C07K 14/475; A61K 8/64; A61K 38/18; A61K 8/983; A61K 35/51; C12N 5/0665; C12N 2501/15
See application file for complete search history.

(56) References Cited

FOREIGN PATENT DOCUMENTS

| | | | |
|---|---|---|---|
| KR | 10-2010-0114729 | A | 10/2010 |
| KR | 10-2017-0093283 | A | 8/2017 |
| WO | 00/05248 | A1 | 2/2000 |
| WO | 2006/002387 | A2 | 1/2006 |

OTHER PUBLICATIONS

Levine et al. Development 133, 209-216, Nov. 2005.*
International Search Report for PCT/KR2021/018355 dated Mar. 10, 2022.
Office Action issued Jun. 21, 2024 in Korean Application No. 10-2021-0173035.
Oriane Guillevic, et al., "A Novel Molecular and Functional Stemness Signature Assessing Human Cord Blood-Derived Endothelial Progenitor Cell Immaturity", PLoS ONE, Apr. 4, 2016, vol. 11, No. 4, pp. 1-20 (20 pages total).
Jianyong Xu, et al., "Chemical-defined medium supporting the expansion of human mesenchymal stem cells", Stem Cell Research & Therapy, 2020, vol. 11, No. 125, pp. 1-11 (11 pages total).

* cited by examiner

*Primary Examiner* — Jeanette M Lieb
(74) *Attorney, Agent, or Firm* — Sughrue Mion, PLLC

(57) ABSTRACT

A method for isolating and culturing umbilical cord blood stem cells that express high levels of GDF-3 is disclosed. Umbilical cord blood stem cells isolated and cultured as described herein exhibit high expression of GDF-3. Stem cells with high expression of GDF-3 maintain high proliferation capacity contrary to conventional stem cells even as passages progress, allowing for the advantage of obtaining a large quantity of healthy stem cells. Furthermore, due to the higher proliferation rate of stem cells, it has been observed that the concentration of extracellular matrix components secreted by the cells is also higher. Therefore, when utilizing GDF-3 high-expressing umbilical cord blood stem cells for the production of cell and culture medium compositions, it is possible to produce raw materials with excellent efficacy and effects.

9 Claims, 6 Drawing Sheets

Figure 1:
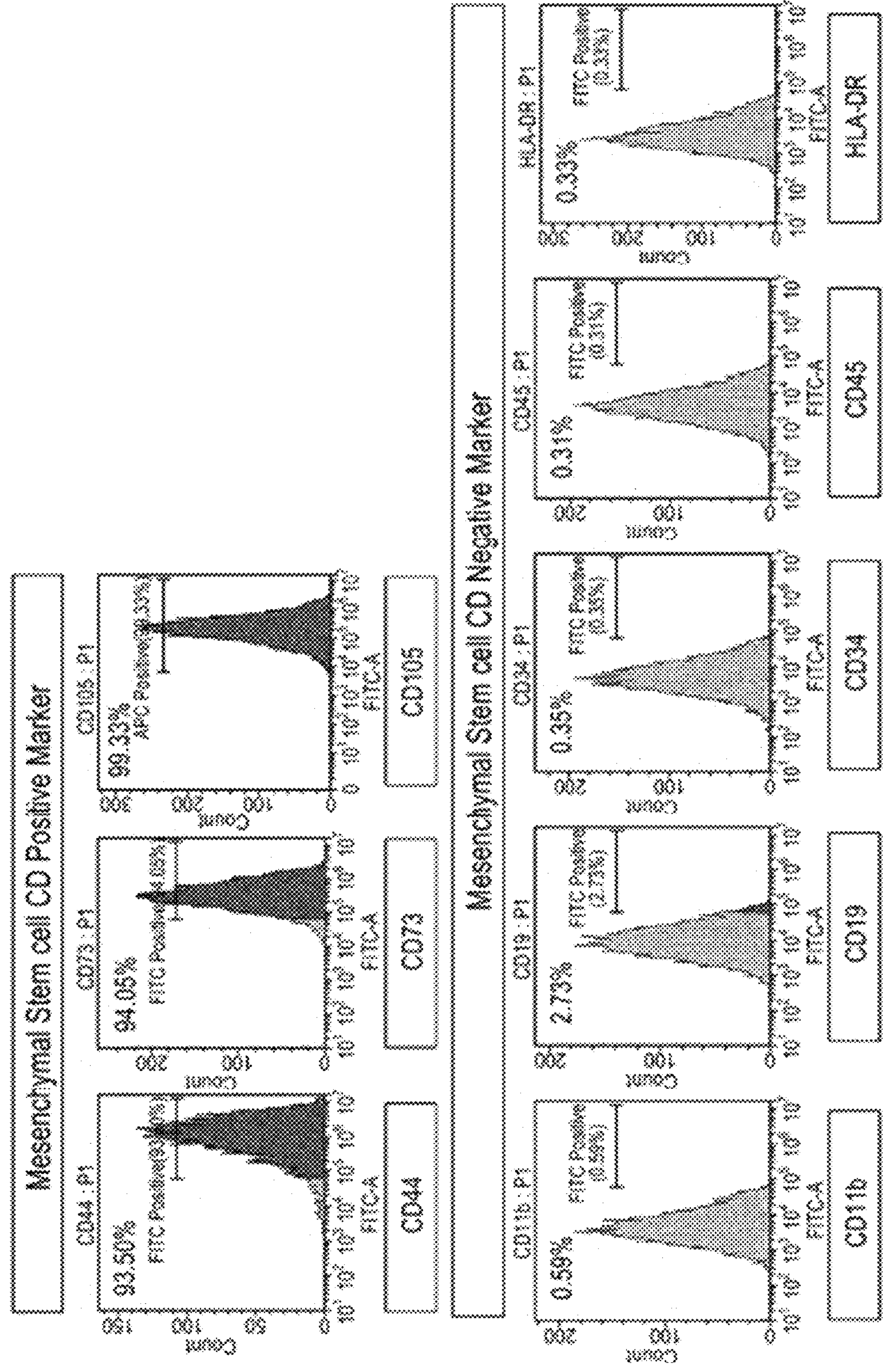

Specification includes a Sequence Listing.

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer, GAPDH forward

<400> SEQUENCE: 1
gacctgccgt ctagaaaaac 20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer, GAPDH reverse

<400> SEQUENCE: 2
ttgaagtcag aggagaccac 20

-continued

```
<210> SEQ ID NO 3
<211> LENGTH: 21
<212> TYPE: DNA
<213> ORGANISM: Artificial Sequence
<220> FEATURE:
<223> OTHER INFORMATION: Synthetic primer, GDF-3 forward

<400> SEQUENCE: 3

agacttatgc tacgtaaagg a                                              21


<210> SEQ ID NO 4
<211> LENGTH: 21
<212> TYPE: DNA
<213> ORGANISM: Artificial Sequence
<220> FEATURE:
<223> OTHER INFORMATION: Synthetic primer, GDF-3 reverse

<400> SEQUENCE: 4

ctttgatggc agacaggtta a                                              21
```

METHOD FOR ISOLATING AND CULTURING CORD BLOOD STEM CELLS EXPRESSING GDF-3 AT HIGH LEVEL, AND USE OF GDF-3

CROSS REFERENCE TO RELATED APPLICATIONS

This Application is a National Stage of International Application No. PCT/KR2021/018355 filed Dec. 6, 2021, claiming priority based on Korean Patent Application No. 10-2020-0168691 filed Dec. 4, 2020.

SEQUENCE LISTING

The content of the electronically submitted sequence listing, file name: Q288104SEQLIST.txt; size: 1,129 bytes; and date of creation: Jun. 1, 2026, filed herewith, is incorporated herein by reference in its entirety.

FIELD OF THE INVENTION

The present invention relates to a method for isolating and culturing umbilical cord blood stem cells that highly express GDF-3, as well as various applications of GDF-3.

BACKGROUND OF THE INVENTION

Animal cell culture involves two main processes: primary culture and subculture. Primary culture refers to the process of isolating and culturing cells from tissue fragments. Subculture, on the other hand, is a method used to maintain cells obtained from primary culture in a continuous manner.

Normal animal cell lines are mortal, meaning they have a limited number of cell divisions. When culturing normal cells, they typically grow as undifferentiated stem cells or precursor cells until the onset of differentiation, at which point their proliferation ceases. In contrast, cells derived from tumor tissues exhibit a mixture of growth and differentiation, allowing them to proliferate continuously.

Subculture, also known as passage or serial passaging, is a method in which cells are periodically transferred to fresh culture dishes every 2-7 days to sustain their proliferation. This process ensures that cells can continue to proliferate by providing them with a new space, as within a limited culture dish, nutrients become depleted, and cell growth is inhibited by the accumulation of metabolic byproducts. In subculture, cells are detached from the culture dish and transferred to a new one since most cells grow as a monolayer and cease proliferation. Additionally, there are methods such as using cell disks or micro-carriers for three-dimensional culture within dedicated culture devices.

Cells derived from animal tissues can undergo continuous cultivation through passages, such as first passage (P1), second passage (P2), third passage (P3), and so on. However, in most cases, when cells are continuously passaged, they eventually reach a point where they no longer proliferate and undergo cell death. Most cells exhibit culture senescence, characterized by changes in cellular properties over time and the manifestation of cellular aging, as the number of divisions increases. Due to these factors, subculture can only be performed for a limited number of passages.

Stem cells are undifferentiated cells that possess the ability to self-renewal and differentiate into various types of tissue cells. They can be classified into embryonic stem cells, adult stem cells, and induced pluripotent stem cells. Embryonic stem cells are derived from the inner cell mass of a blastocyst and exhibit pluripotency, meaning they can differentiate into any cell or tissue in the body. While they have potential therapeutic applications, there are ethical concerns and a high risk of tumor formation associated with their transplantation. Induced pluripotent stem cells are generated by introducing specific genes into adult somatic cells to induce a pluripotent state similar to embryonic stem cells. They address the ethical concerns associated with embryonic stem cells, but their reprogramming efficiency is low, and there are risks associated with gene delivery using viruses, limiting their practical use for clinical therapies. Adult stem cells, also known as somatic stem cells, exist in mature tissues and play a role in replenishing or repairing damaged cells. Unlike embryonic stem cells, they are more stable in their differentiation potential, have a lower risk of tumor formation, and do not raise ethical concerns as they do not involve the destruction of embryos.

Adult stem cells can be harvested from various sources such as adipose tissue, bone marrow, and peripheral blood. Adipose-derived and bone marrow-derived stem cells are collected using invasive methods from donors, and the function and efficacy of the stem cells may vary depending on the donor's age and health status. On the other hand, peripheral blood stem cells are obtained from discarded peripheral blood without invasive procedures, and since similar gestational age (40 weeks) peripheral blood is used, there is minimal difference in the function and efficacy of stem cells between donors.

Many cell-based therapies utilizing the regenerative and anti-inflammatory properties of adult stem cells are being developed. The mechanisms behind the regenerative and anti-inflammatory effects of adult stem cells involve the substances produced by these cells, including proteins such as collagen, TGF-β1, and miRNA. However, the effectiveness of stem cell-based therapies is limited by issues such as cell engraftment and the incomplete resolution of tumor formation. To address these challenges, research on stem cell culture media and extracellular vesicles is actively conducted.

Mesenchymal stem cells (MSCs) are undifferentiated adult stem cells that exist among the differentiated cells in tissues and organs. They possess the ability to self-renewal, meaning they can proliferate on their own. MSCs can easily proliferate in vitro and have the potential to differentiate into various cell types, including adipocytes, osteocytes, chondrocytes, and myocytes, making them valuable for tissue regeneration through their differentiation capabilities.

MSCs are known to secrete various growth factors and cytokines, such as epithelial growth factor (EGF) and fibroblast growth factor (FGF), which promote collagen synthesis by fibroblasts. This secretion of growth factors and cytokines plays a crucial role in skin regeneration.

Furthermore, it is possible to improve the suitability of mesenchymal stem cells (MSCs) isolated from the human body for therapeutic purposes. The various growth factors or proteins secreted by stem cells can be utilized for immunomodulation, anti-inflammatory effects, and application in diverse diseases.

The wide range of growth factors or proteins released from stem cells can also find industrial applications in fields such as medicine and cosmetics. However, the technology to achieve high concentrations of growth factors in stem cell culture supernatant or stem cell-derived compositions is still underdeveloped. There is a need for novel methods to manufacture culture media or compositions containing high concentrations of growth factors to promote the synthesis of extracellular matrix.

The extracellular matrix (ECM) is a structural component formed by various substances secreted by cells, filling the space between cells and connecting them to the surrounding tissues. The ECM not only provides structural support for cells and intercellular connections but also plays important roles in cell communication, including signal transduction, as well as embryonic development and cell differentiation. Fundamentally, the ECM consists of water, proteins, carbohydrates, and each tissue possesses its own unique composition and organization of ECM from the onset of development. The interaction between the ECM and cells occurs through cell surface receptors such as integrins, discoidin domain receptors, and syndecans, allowing the linkage between the cell cytoskeleton and the ECM. Furthermore, the ECM has a highly dynamic structure and undergoes continuous remodeling. The physical and biochemical properties of the ECM contribute to the unique mechanical characteristics, such as tensile strength and elasticity, of organs within organisms. The ECM is composed of two major macromolecules: proteoglycans (PGs), which are complexed with proteins and carbohydrates, and fibrous proteins, such as collagen and keratin, which are insoluble in water.

Proteoglycans are the most abundant substances found between cells and tissues, existing in the form of a hydrated gel. They play various roles utilizing properties such as buffering, hydration, binding, and resistance.

Collagen, which is the most abundant protein among the different types of fibrous proteins, constitutes approximately 30% of total protein in multicellular animals. Collagen is responsible for the structural framework of the extracellular matrix, contributes to elasticity, cell attachment mechanisms, cell migration, and tissue development. It is also interconnected with another fibrous protein called elastin. Elastin fibers are involved in the elasticity of tissues that require repetitive stretching. However, the extensibility of elastin fibers is limited due to their close association with collagen fibers. Another fibrous protein called fibronectin (FN) is present, which organizes the space between the extracellular matrix and is responsible for the connection between cells and the extracellular matrix.

The stem cell marker GDF-3 (Growth Differentiation Factor-3) belongs to the TGF-β superfamily and activates Nodal signaling, thereby promoting the transcriptional activity of skin-regenerating proteins such as collagen, fibronectin, and TGF-BI. The correlation between GDF-3 and stem cells has primarily been studied in embryonic stem cells (ESCs), where GDF-3 is known as a marker of stemness. However, its function in adult stem cells and other types of stem cells remains unknown.

BRIEF SUMMARY OF THE INVENTION

The present invention aims to provide a method for producing umbilical cord blood stem cells that highly express GDF-3 gene, as well as various applications of GDF-3.

Specifically, the present invention aims to provide a method for isolating high-potency umbilical cord blood-derived stem cells, characterized by utilizing a newly designed stem cell culture medium in fibronectin-coated culture plates to obtain rapidly proliferating stem cells from mononuclear cells isolated from umbilical cord blood. Furthermore, the present invention aims to provide a method for enhancing cell proliferation and secretion of extracellular matrix components by inducing increased expression of GDF-3 within stem cells. Additionally, based on this, the present invention seeks to induce cell proliferation and secretion of extracellular matrix components using GDF-3 high-expressing umbilical cord blood stem cells, thereby providing a culture medium composition containing extracellular matrix components.

A first aspect of the present invention provides a method of producing GDF-3, which is characterized by culturing umbilical cord blood stem cells to induce GDF-3 expression.

A second aspect of the present invention provides a method of producing GDF-3-expressing umbilical cord blood stem cells, wherein umbilical cord blood stem cells with a fast cell doubling time are isolated and cultured to obtain umbilical cord blood stem cells that express GDF-3 at high levels.

A third aspect of the present invention provides GDF-3-expressing umbilical cord blood stem cells, which have been obtained by seeding isolated mononuclear cells from umbilical cord blood onto a culture dish containing a medium supplemented with TGF-β superfamily growth factors and then selectively culturing cells based on their attachment to the culture dish and their relative fast proliferation rate.

A fourth aspect of the present invention provides a composition for promoting fibroblast growth comprising GDF-3.

A fifth aspect of the present invention provides a composition for skin regeneration, comprising GDF-3.

BRIEF DESCRIPTION OF THE DRAWINGS/FIGURES

FIG. 1 represents the analysis of whether isolated and cultured umbilical cord blood stem cells express specific surface proteins in Example 1.

Figure 2:
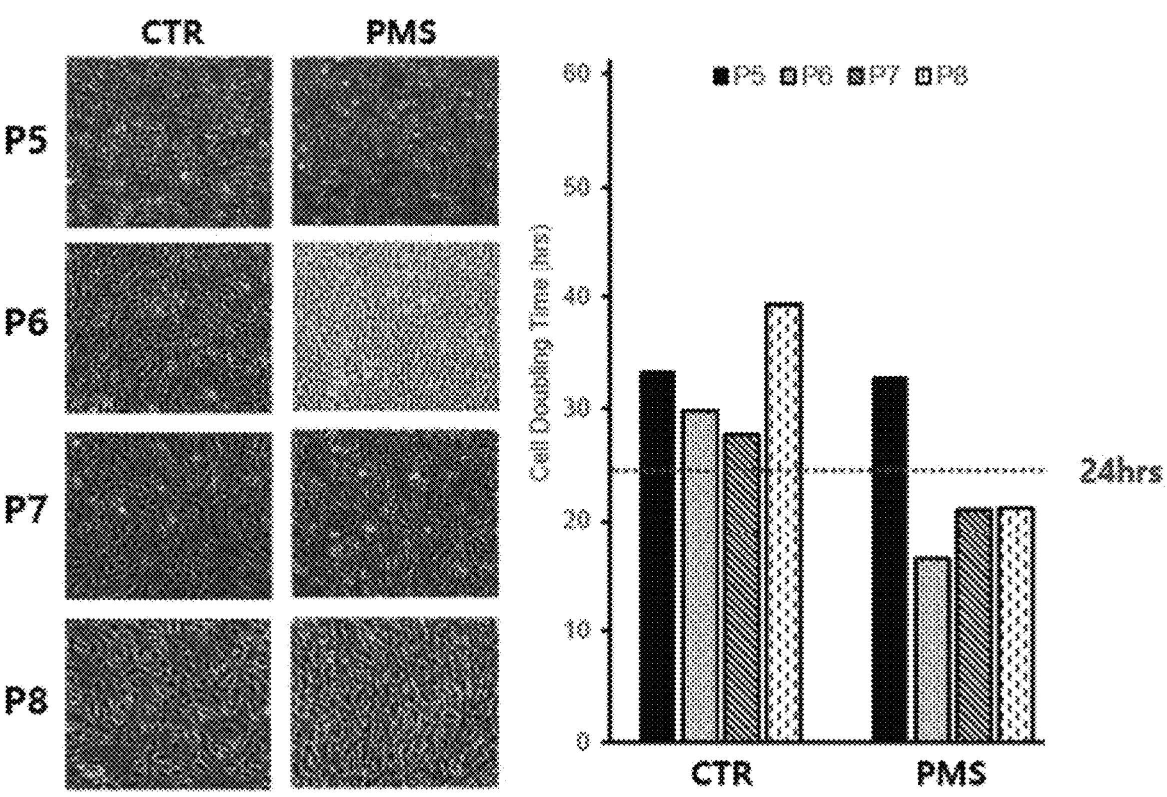

FIG. 2 compares the morphology and proliferation rate of umbilical cord blood stem cells after isolation using regular DMEM medium (CTR) and a novel stem cell culture medium (PMS).

Figure 3:
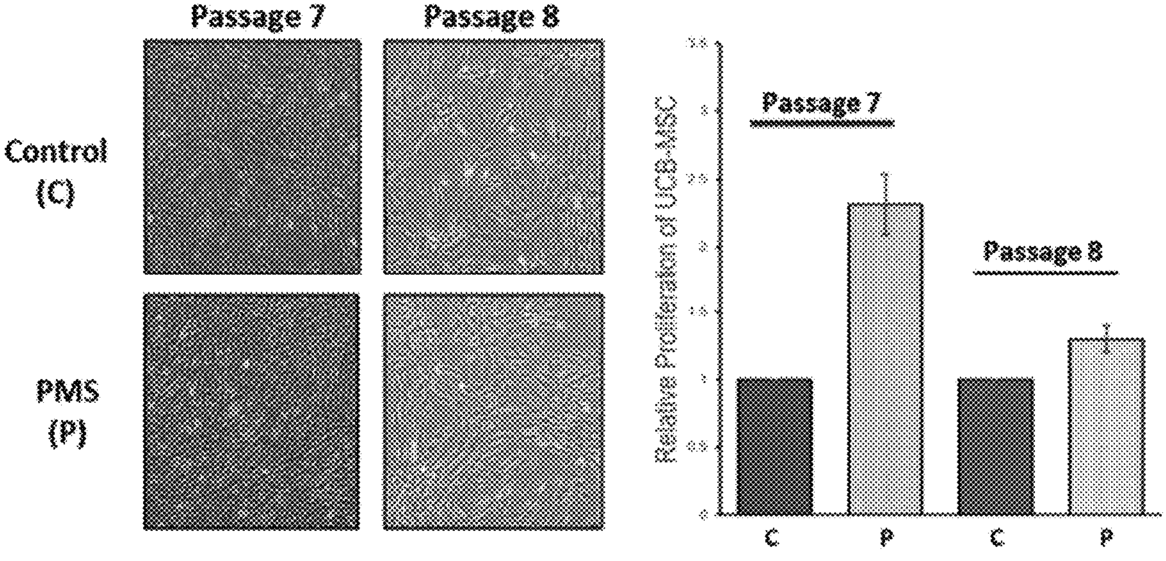

FIG. 3 compares the proliferation levels of cells at the late passage (after P7) between regular DMEM medium (CTR) and the novel stem cell culture medium (PMS).

Figure 4:
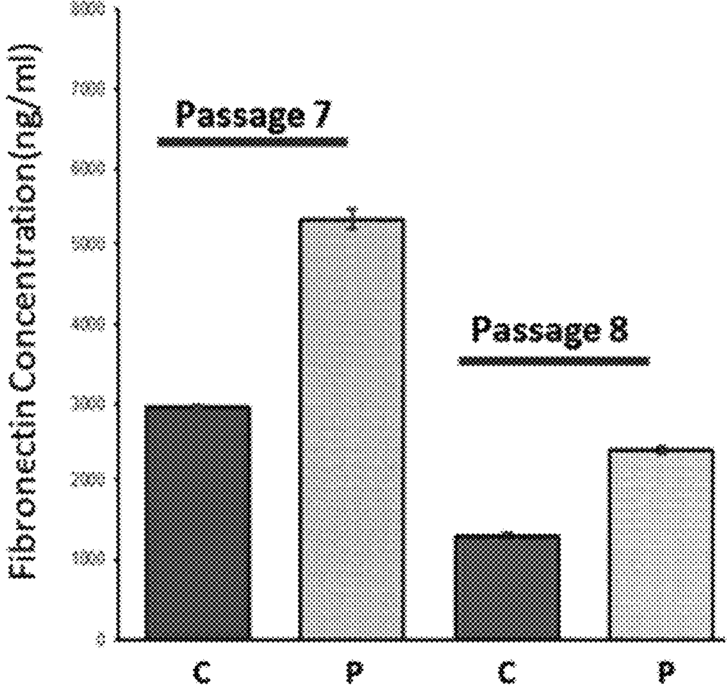

FIG. 4 compares the secretion of extracellular matrix substance, fibronectin, by umbilical cord blood stem cells cultured in regular DMEM medium (CTR) and the novel stem cell culture medium (PMS).

Figure 5:
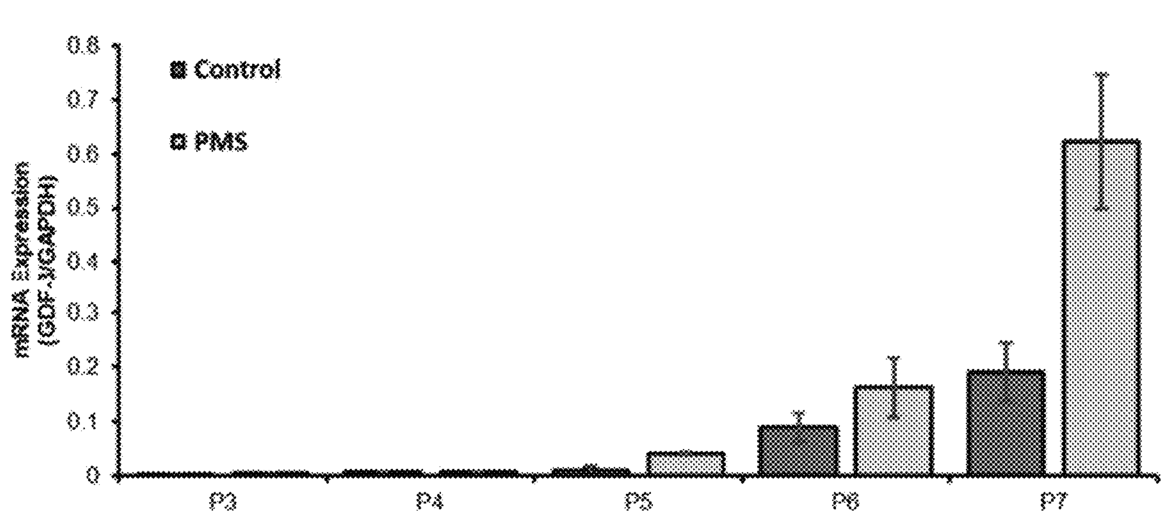

FIG. 5 analyzes the gene expression pattern of GDF-3 in umbilical cord blood stem cells cultured in regular DMEM medium (CTR) and the novel stem cell culture medium (PMS) from the early passage (P3) to the late passage (P7).

Figure 6:
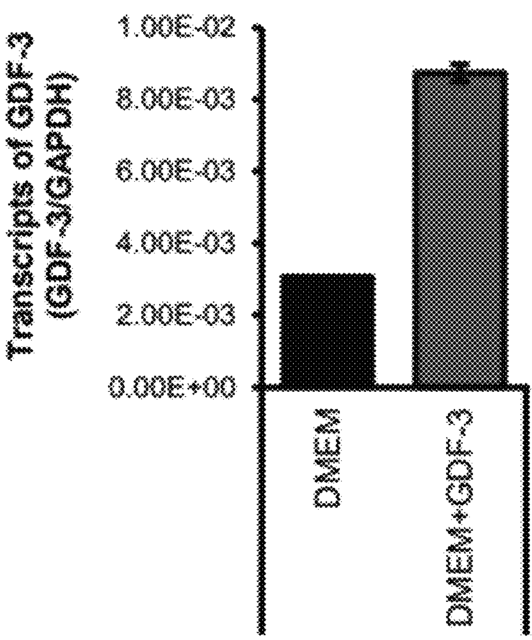

FIG. 6 demonstrates the confirmation of high expression of GDF-3 gene in regular dermal fibroblast cells after GDF-3 protein treatment.

Figure 7:
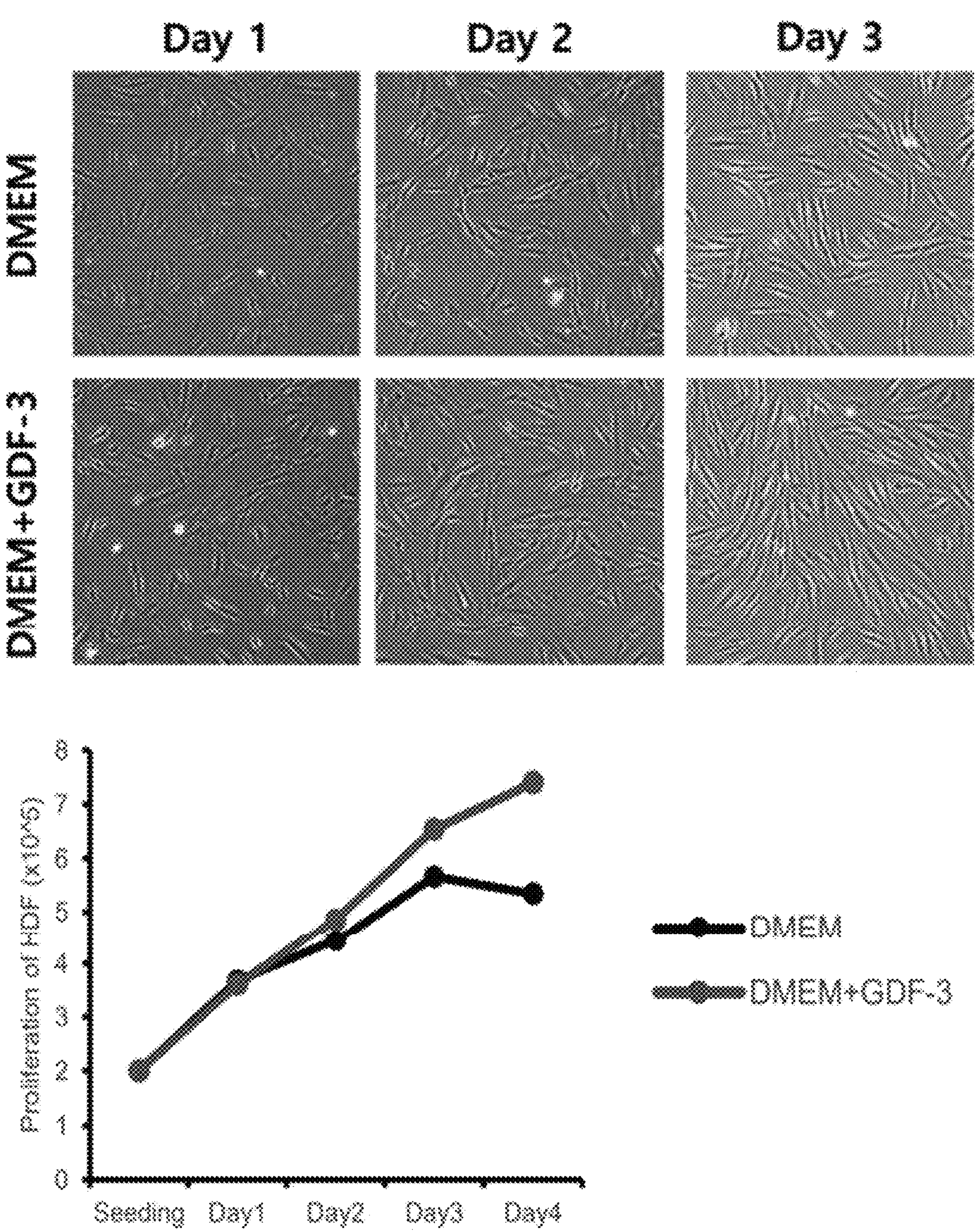

FIG. 7 illustrates the impact of GDF-3 on the growth of human dermal fibroblast (HDF) cells. It shows that HDF cells with high expression of GDF-3 exhibit faster and sustained cell proliferation.

Figure 8:
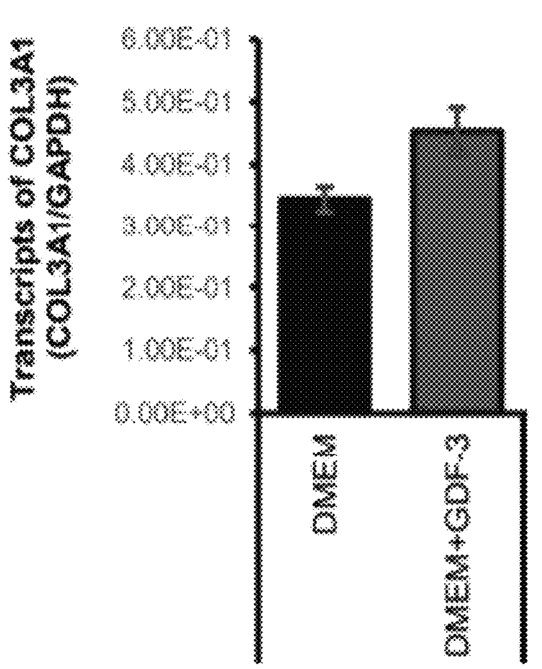
Figure 8:
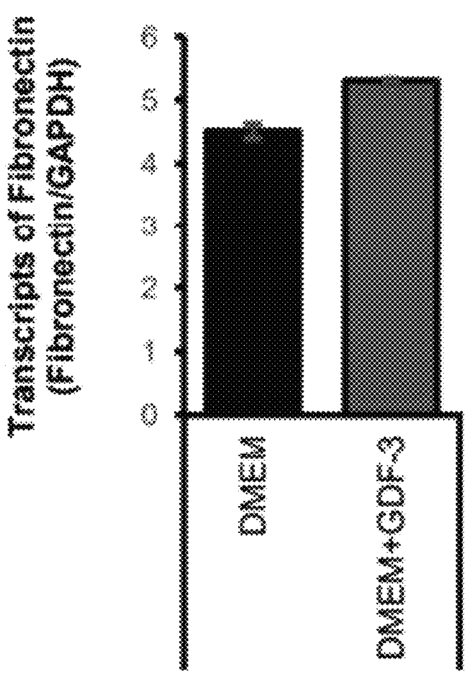

FIG. 8 confirms that high expression of GDF-3 in regular skin cells leads to increased gene expression of collagen and fibronectin, which are components of the extracellular matrix, compared to the control group.

DETAILED DESCRIPTION OF THE INVENTION

The inventors have conducted various experiments considering the need to obtain a large quantity of stem cells for easy establishment of a master cell bank, and the possibility of obtaining a large amount of cells and culture medium containing high levels of active ingredients. Based on these experiments, they discovered the following:

(i) High expression of GDF-3 promotes the synthesis of effective substances involved in cell proliferation and regeneration. (ii) There is a correlation between the expression level of GDF-3 in isolated and cultured umbilical cord blood stem cells and their proliferation rate. (iii) Gene expression of GDF-3 is significantly higher in umbilical cord blood stem cells. (iv) Treatment of human dermal fibroblasts (HDF) with GDF-3 results in elongated and shorter cell morphology, which is favorable for cell proliferation and sustained growth (Example 5 and FIG. 7). (v) Treatment of HDF with GDF-3 leads to increased gene expression of skin components such as collagen and fibronectin, which are involved in skin regeneration (Example 6 and FIG. 8).

Based on these findings, the present invention has been completed.

According to the present invention, isolated and cultured umbilical cord blood stem cells exhibit the characteristic of high expression of GDF-3. Typically, as the passages progress, the proliferation of stem cells decreases, making it difficult to obtain a sufficient quantity of cells. However, in the case of stem cells expressing high levels of GDF-3, their proliferation capacity remains higher compared to the control group even as passages progress, allowing for the mass amount secure of healthy stem cells. Additionally, the high proliferation rate of stem cells leads to increased concentration of extracellular matrix components secreted by the cells. Therefore, when producing a culture medium composition utilizing umbilical cord blood stem cells with high expression of GDF-3, it is possible to produce raw materials with excellent efficacy and effects due to the higher concentration of bioactive substances.

The method of isolating and culturing stem cells with high expression of GDF-3 according to an aspect of the present invention is characterized by the use of a newly designed stem cell culture medium. In this case, the newly designed stem cell culture medium incorporates various growth factors, including those from the TGF-β superfamily.

The present invention enables the isolation and cultivation of umbilical cord blood stem cells with a cell doubling time of less than 24 hours.

As confirmed in the present invention, GDF-3 can promote the growth of fibroblasts (FIG. 8). Human dermal fibroblasts are an unrestricted example of fibroblasts whose growth can be increased by GDF-3.

Furthermore, as observed in the present invention, GDF-3 can increase the expression of GDF-3, collagen, and/or fibronectin genes in fibroblasts (FIG. 8).

Based on the discovery that the expression level of GDF-3 in isolated and cultured umbilical cord blood stem cells is correlated with their proliferation rate, the method for producing GDF-3-expressing umbilical cord blood stem cells in accordance with an aspect of the present invention involves the isolation and cultivation of umbilical cord blood stem cells with a fast cell doubling time to secure umbilical cord blood stem cells highly expressing GDF-3.

The higher the proliferation rate of the isolated and cultured umbilical cord blood stem cells, the higher the expression level of GDF-3.

Therefore, the present invention enables the establishment of a cell bank for umbilical cord blood stem cells highly expressing GDF-3. For example, the method involves seeding the isolated mononuclear cells from umbilical cord blood onto a culture medium containing TGF-β superfamily growth factors, selectively isolating and culturing mononuclear cells that attach to the culture dish and proliferate relatively rapidly, resulting in the establishment of a cell bank for GDF-3-high expressing umbilical cord blood stem cells.

Furthermore, the method for producing GDF-3-high expressing umbilical cord blood stem cells according to an aspect of the present invention is characterized by isolating and culturing umbilical cord blood stem cells with a fast cell doubling time in a culture medium (Example 1).

According to one embodiment, the method for producing GDF-3-expressing umbilical cord blood stem cells includes a first step of seeding the isolated mononuclear cells from umbilical cord blood into a culture medium containing TGF-β superfamily growth factors and cultivating them; and a second step of selectively isolating and culturing mononuclear cells that attach to the culture dish and proliferate relatively rapidly.

In the second step, only the attached mononuclear cells can be cultured, while the cells that do not attach to the culture dish can be removed.

The GDF-3-expressing umbilical cord blood stem cells produced according to the present invention are capable of differentiating into adipocytes, chondrocytes, and/or osteocytes. Therefore, umbilical cord blood stem cells highly expressing GDF-3 can be used as cellular therapeutics.

The types, combinations, and concentrations of growth factors produced during stem cell culture vary depending on the origin and culture method of the stem cells. Thus, the GDF-3-expressing umbilical cord blood stem cells produced according to the present invention can be cultured to produce a GDF-3-containing culture medium. In particular, the present invention enables the isolation and culturing of umbilical cord blood-derived stem cells highly expressing GDF-3 for the production of GDF-3-containing culture medium.

Surprisingly, it was discovered that the expression level of GDF-3 in the umbilical cord blood stem cells produced according to the present invention gradually increases as passages progress (FIG. 5). Therefore, in order to obtain umbilical cord blood stem cells highly expressing GDF-3, GDF-3-expressing umbilical cord blood stem cells from passage 5 to passage 7 or higher can be used (FIG. 3).

The method for producing GDF-3-expressing umbilical cord blood stem cells according to one embodiment of the present invention is characterized by isolating and culturing umbilical cord blood stem cells in a medium containing TGF-β superfamily growth factor. In this case, superior GDF-3-expressing umbilical cord blood stem cells can be obtained through serial culturing, ensuring their robust growth ability. Therefore, the method for producing GDF-3-expressing umbilical cord blood stem cells according to an aspect of the present invention involves isolating and culturing umbilical cord blood stem cells in a medium containing various growth factors, including TGF-β superfamily, and subsequently expanding the umbilical cord blood stem cells to obtain a large quantity through passages (FIG. 3).

By serially culturing GDF-3-expressing umbilical cord blood stem cells according to an aspect of the present invention, it is possible to obtain a large quantity of umbilical cord blood stem cells with superior secretion ability of extracellular matrix components (FIG. 4).

As mentioned, the stem cell marker GDF-3 belongs to the TGF-β superfamily. TGF-β is a pleiotropic factor and exhibits characteristics of a multifunctional growth factor.

TGF-β (Transforming growth factor-β) signaling plays a crucial role in various biological processes and performs diverse functions such as cell growth inhibition, apoptosis, differentiation, and epithelial-mesenchymal transition (EMT). The TGF-β signaling pathway is tightly regulated and plays a critical role in maintaining cellular homeostasis, as well as in development and organ formation. Disruption of TGF-β signaling can lead to life-threatening conditions such as cancer, fibrosis, and congenital malformations.

TGF-β initially exhibits tumor-suppressive activity in the early stages of carcinogenesis but is known to promote tumor growth in later stages. TGF-β1 is abundantly expressed in most cancer tissues, and its high expression is associated with malignancy and poor prognosis in cancer patients.

Secreted TGF-β binds to a heteromeric complex composed of two types of receptors, type I and type II receptors, initiating signaling. When TGF-β binds to the type II receptor, the type I receptor recognizes it and forms a complex with the type II receptor, leading to phosphorylation of the GS domain of the type I receptor by the type II receptor. Phosphorylated TGF-type I receptor activates downstream mediators of TGF-β signaling, such as Smad2 and Smad3, by phosphorylating their C-terminal serine residues. Activated Smad2 and Smad3 form a complex with Smad4 and translocate to the nucleus, where they participate in the expression of target genes.

The tumor-suppressive role of TGF-β has been demonstrated in various studies. Conversely, TGF-β promotes tumor growth, invasion, and metastasis at later stages of cancer progression. The detailed molecular mechanisms underlying the switch in the role of TGF-β during these opposing processes of cancer progression have not yet been clearly elucidated.

TGF-β is known to play a crucial role as an executor in determining immune homeostasis and tolerance by inhibiting the function and expansion of various components of the immune system. TGF-β regulates immune tolerance and inflammatory responses. The TGF-β signaling directly suppresses the cytotoxic program of CD8+ T cells.

In the tumor microenvironment, excessive production of TGF-β1 by cancer cells leads to significant alterations in the signaling cascade of cancer cells. These changes negatively impact the interaction between cancer cells and the tumor stroma. When cross-talk between cells is disrupted, it creates a permissive stroma that facilitates the spread of tumor cells. TGF-β secreted by cancer cells induces the transition to epithelial-mesenchymal transition (EMT) and promotes the generation of cancer stem cells (CSC)-like cells, which possess similar characteristics to CSCs.

Cells undergoing EMT acquire an increased migratory ability, making them prone to undergo metastasis. These cells undergo morphological changes, adopting a spindle-shaped morphology, and undergo alterations in the cytoskeleton, enabling them to easily migrate to other organs, facilitating metastasis.

In epithelial cells, EMT is characterized by the loss of E-cadherin, a protein necessary for epithelial cell adhesion, and an increase in the expression of mesenchymal markers such as N-cadherin, vimentin, and fibronectin. TGF-β serves as a key mediator of EMT by activating various transcription factors, including SNAI1/2, Twist, and ZEB1/2. Tumor cells undergoing EMT acquire cancer stem cell (CSC) properties.

Similarly, TGF-β, a pleiotropic factor and multifunctional growth factor, plays contrasting roles in the progression of cancer, and the detailed molecular mechanisms underlying this role switch are still not fully understood. Therefore, considering the potential for similar side effects, GDF-3, which is a member of the TGF-β superfamily, may also pose similar risks. Hence, it is desirable to use GDF-3 produced in large quantities through the in vitro cultivation of isolated umbilical cord blood stem cells according to the present invention. By controlling the timing, site, and dosage of GDF-3 administration, it can be applied effectively in vivo.

In this specification, the term "culture medium" refers to a composition that contains essential components necessary for the growth and proliferation of cells in vitro. It encompasses stem cell culture media commonly used in the field, including but not limited to DMEM (Dulbecco's Modified Eagle's Medium), MEM (Minimal Essential Medium), BME (Basal Medium Eagle), RPMI 1640, DMEM/F-10 (Dulbecco's Modified Eagle's Medium: Nutrient Mixture F-10), DMEM/F-12 (Dulbecco's Modified Eagle's Medium: Nutrient Mixture F-12), α-MEM (α-Minimal essential Medium), G-MEM (Glasgow's Minimal Essential Medium), IMDM (Isocove's Modified Dulbecco's Medium), KnockOut DMEM, commercially manufactured media, or artificially synthesized media. The culture medium typically contains carbon sources, nitrogen sources, and trace elements, and may also include amino acids, antibiotics, and other additives.

Furthermore, as confirmed in the present invention, GDF-3 can stimulate the synthesis of effective substances that increase the expression of at least one selected gene(s) encoding proteins such as GDF-3, collagen, and fibronectin in fibroblasts, thereby promoting cell proliferation and/or regeneration. Therefore, it can be used as an active ingredient in compositions for fibroblast growth and proliferation (FIGS. 6-8). Human Dermal Fibroblasts (HDF) represent an example of fibroblasts without limitation.

Therefore, according to the present invention, GDF-3 can be used as an effective ingredient in compositions for skin regeneration.

Examples of compositions for skin regeneration include cosmetic compositions for skin regeneration or wrinkle improvement, dermatological compositions for topical administration, and pharmaceutical compositions for skin regeneration or wrinkle treatment. The pharmaceutical compositions of the present invention may include pharmaceutically acceptable salts of the aforementioned active ingredients.

"Skin regeneration" refers to the recovery of skin tissue from damage caused by external and internal factors. External factors may include ultraviolet radiation, external pollutants, wounds, injury, etc., while internal factors may include stress, etc.

"Skin wrinkles" refer to fine lines or creases that appear on the skin and can be caused by genetic factors, a decrease in collagen and elastin present in the dermis, and external environmental factors.

"Wrinkle improvement" refers to the inhibition or reduction of the formation of wrinkles on the skin or the alleviation of already existing wrinkles. In the context of the present invention, skin regeneration and wrinkle improvement may include the enhancement of skin elasticity.

"Wrinkle treatment" refers to at least partially or temporarily halting the formation of wrinkles on the skin.

"Skin elasticity" is manifested by elastic fibers composed of elastin in the dermal layer. These elastic fibers have a very low elastic modulus, similar to rubber, allowing them to deform easily under minimal force and return to their original shape when the force is removed. Additionally, elastic fibers have a structure where microfibrils are embedded in an amorphous matrix called elastin. Elastin is a protein consisting of highly unique amino acids derived from lysine, including desmosine and isodesmosine, which are found exclusively in elastic fibers. Desmosine and isodesmosine form cross-links within long peptide chains, conferring rubber-like properties to elastin.

"Promotion of skin elasticity" refers to the maintenance or increase in skin elasticity when elastic fibers composed of elastin coexist with collagen, known as connective fibers, in sufficient amounts.

When the aforementioned active ingredients are used in cosmetic compositions, they can be formulated in various forms of emulsion and dispersion. For example, they can be formulated as lotions such as fluid lotions or nourishing lotions, liquids such as facial lotions or body lotions, creams such as nutrient creams, moisturizing creams, eye creams, essences, sprays, gels, masks, sunscreens, makeup bases, liquid or powder type of makeup removers such as cleansing creams, cleansing lotions, cleansing oils, cleansing foams, soaps, body washes, and other types of cleansers commonly used in the field.

Additionally, the cosmetic compositions may contain, in addition to the active ingredients, fatty substances, organic solvents, solubilizers, thickeners, emollients, antioxidants, suspending agents, stabilizers, foaming agents, fragrances, surfactants, water, ionic or non-ionic emulsifiers, fillers, metal ion chelating agents, preservatives, vitamins, sunscreens, humectants, essential oils, dyes, pigments, hydrophilic or lipophilic active agents, lipid vesicles commonly used in the field of cosmetics, and other additives commonly used in the field of cosmetic science.

When the aforementioned active ingredients are used in dermatological formulations, in addition to the active ingredients, they may contain fatty substances, organic solvents, solubilizers, thickeners, emollients, antioxidants, suspending agents, stabilizers, foaming agents, fragrances, surfactants, water, ionic or non-ionic emulsifiers, fillers, metal ion chelating agents, preservatives, vitamins, sunscreens, humectants, essential oils, dyes, pigments, hydrophilic or lipophilic active agents, lipid vesicles, or other additives commonly used in the field of dermatology. Moreover, these ingredients can be introduced in amounts commonly used in the field of dermatological formulations.

Furthermore, although not limited to, when the aforementioned active ingredients are provided in the form of dermatological formulations, they can take the form of ointments, patches, gels, creams, or sprays, among others.

The pharmaceutically acceptable salts of the aforementioned active ingredient can include organic or inorganic acid addition salts. Examples of organic acids include formic acid, acetic acid, propionic acid, lactic acid, butyric acid, isobutyric acid, trifluoroacetic acid, malic acid, maleic acid, malonic acid, fumaric acid, succinic acid, succinic acid monoamide, gluconic acid, tartaric acid, oxalic acid, citric acid, glycolic acid, glucuronic acid, ascorbic acid, benzoic acid, phthalic acid, salicylic acid, anthranilic acid, dichloroacetic acid, aminoxyacetic acid, benzene sulfonic acid, p-toluenesulfonic acid, and methanesulfonic acid derivatives. Inorganic acids can include hydrochloric acid, bromic acid, sulfuric acid, phosphoric acid, nitric acid, carbonic acid, and sulfonic acid derivatives. Preferably, the salts can be in the form of hydrochloride or acetate, and more preferably in the form of hydrochloride.

The mentioned acid addition salts are prepared by a) directly mixing the active ingredient with the acid, b) dissolving and mixing either one in a solvent or aqueous solvent, or c) placing the active ingredient in a solvent or aqueous solvent with the acid and mixing them using conventional salt preparation methods.

In addition, other possible salt forms include gabapentin salts, gabapentin enacarbil salts, pregabalin salts, nicotinic acid salts, adipate salts, hemimalonate salts, cysteine salts, acetylcysteine salts, methionine salts, arginine salts, lysine salts, ornithine salts, aspartic acid salts, and so on.

In addition, when using the active ingredient of the present invention as a pharmaceutical, it can contain one or more additional active ingredients that exhibit similar or identical functions. For example, it may include already known skin regeneration or wrinkle-improving components. By incorporating additional ingredients for skin regeneration or wrinkle improvement, the effects of skin regeneration or wrinkle improvement of the present invention's culture conditioned media can be further enhanced. When adding these ingredients, considerations can be made for skin safety in combination use, ease of formulation, and stability of active ingredients. The additional ingredients can be included in the total composition in a range of 0.0001% to 10% by weight, and the inclusion range can be adjusted according to factors such as skin safety and ease of formulation with the active ingredient.

Furthermore, the pharmaceutical composition of the present invention can include other pharmaceutically acceptable excipients.

Pharmaceutically acceptable excipients can include various components such as buffer solutions, sterile injection water, normal saline or phosphate buffer saline, sucrose, histidine, salts, and polysorbate.

The pharmaceutical composition of the present invention can be administered orally or non-orally (e.g., transdermally). It can be formulated in various dosage forms for oral and non-oral administration during clinical use. When formulating, commonly used diluents or excipients such as fillers, disintegrants, binders, lubricants, solubilizers, surfactants, etc., can be used.

Solid formulations for oral administration can include tablets, powders, granules, capsule formulations, etc. These solid formulations can be formulated by mixing at least one excipient such as starch, calcium carbonate, sucrose, or lactose, and gelatin.

In addition to simple excipients, lubricants such as magnesium stearate and talc can also be used. Liquid formulations for oral administration can include suspensions, emulsions, syrups, etc. In addition to common diluents such as water and liquid paraffin, various excipients such as moistening agents, sweeteners, flavoring agents, preservatives, etc., can be included.

Formulations for non-oral administration can include sterilized aqueous solutions, non-aqueous solvents, suspensions, emulsions, freeze-dried formulations, suppositories, etc. Non-aqueous solvents and suspending agents such as propylene glycol, polyethylene glycol, vegetable oils such as olive oil, injectable esters such as ethyl oleate, can be used. Bases for suppositories can include witepsol, macrogol, tween 61, cocoa butter, laurin, and glycerol gelatin.

In the present invention, adult stem cells that highly express GDF-3 are isolated from umbilical cord blood, and the role of GDF-3 in umbilical cord blood stem cells is analyzed. The results have shown that umbilical cord blood stem cells with high expression of GDF-3 exhibit increased cell proliferation ability and extracellular matrix secretion. Furthermore, it has been discovered that GDF-3 influences cell proliferation and extracellular matrix secretion in not only stem cells but also somatic cells.

Based on these characteristics, as the potential for expansion of adult stem cells through passages increases, it becomes possible to obtain a larger quantity of stem cells and secure a significant amount of effective substances secreted by stem cells. This can be beneficial for the development of various compositions utilizing GDF-3-high expressing umbilical cord blood stem cells and the secreted substances by stem cells.

Therefore, the GDF-3-high expressing umbilical cord blood stem cells produced according to the present invention can be utilized as a key ingredient in the field of next-generation biopharmaceuticals.

Moreover, when the secretion of extracellular matrix is increased by GDF-3, the efficacy of cell culture conditioned media containing such factors is enhanced. This can be advantageous in the development of compositions applicable to cosmetics and pharmaceuticals, where the culture media can be utilized.

Hereinafter, the present invention will be described in more detail through examples. These examples are for illustrative purposes only, and it will be apparent to those of ordinary skill in the art that the scope of the present invention is not construed as being limited by these examples.

Example 1. Umbilical Cord Blood Stem Cell Isolation 1.1. Isolation of Umbilical Cord Blood Mononuclear Cells Umbilical cord blood obtained from the mother was mixed with Hetasep™ to remove red blood cells. The remaining mononuclear cells were isolated by processing the sample with Ficoll-plaque and subjected to centrifugation. The isolated umbilical cord blood mononuclear cells were washed with PBS. The cells were seeded onto culture dishes coated with fibronectin (50 g/ml), which had been pre-coated for 24 hours at 4° C. A novel self-developed culture medium, consisting of DMEM/F12 supplemented with FGF-2, EGF, TGF-β superfamily growth factors, ascorbic acid, and heparin, was used for the culture.

1.2. Isolation of Umbilical Cord Blood Stem Cells

After 48 hours of culture, non-adherent cells were removed, and only the adherent mononuclear cells were cultured. The rapidly proliferating mononuclear cells were selectively isolated and cultured. The culture medium was replaced every 2-3 days, and umbilical cord blood stem cells with a cell doubling time of less than 24 hours were isolated. The stem cell marker was analyzed.

1.3. Analysis of Surface Marker Expression in Umbilical Cord Blood Stem Cells

Following the isolation of umbilical cord blood stem cells in step 1.2., flow cytometry experiments were performed to confirm whether the isolated cells were umbilical cord blood stem cells. For surface antigen phenotyping, 3-4 passages of cells were obtained, stained with fluorescein isothiocyanate (FITC) or phycoerythrin (PE)-conjugated antibodies, and analyzed using FACS (CytoFLEX, BECKMAN COULTER, CA).

To analyze the characteristics of the isolated umbilical cord blood stem cells from step 1.2., positive surface markers such as CD44 (mesenchymal stem cell marker), CD73 (mesenchymal stem cell marker), and CD105 (mesenchymal stem cell marker) were used. Negative surface markers including CD11b (hematopoietic progenitor cell marker), CD19 (immune cell marker), CD34 (hematopoietic progenitor cell marker), CD45 (non-hematopoietic stem cell marker), and HLA-DR (immune response-related marker) were also used. The results showed the percentage of positive cells for CD antigens of umbilical cord blood stem cells, as shown in Table 1 and represented graphically in FIG. 1.

TABLE 1

| Types of CD antigens | | the percentage (%) of cells positive for the CD antigens |
|---|---|---|
| Positive antigens of umbilical cord blood stem cells | CD44 | 93.50% |
| | CD73 | 94.05% |
| | CD105 | 99.33% |
| Negative antigens of umbilical cord blood stem | CD11b | 0.59% |
| | CD19 | 2.73% |
| | CD34 | 0.35% |
| | CD45 | 0.31% |
| | HLA-DR | 0.33% |

Comparative Example 1

For the isolation of mononuclear cells from umbilical cord blood (1.1) and the subsequent isolation of umbilical cord blood stem cells (1.2), the same method as Example 1 was followed, except for the use of DMEM as the control medium instead of the novel self-developed stem cell culture medium.

Example 2. Umbilical Cord Blood Stem Cell Culture and Proliferation Analysis

The umbilical cord blood stem cells isolated from Example 1 and Comparative Example 1 were cultured in a novel stem cell culture medium based on DMEM/F12 supplemented with 10% fetal bovine serum (FBS) and fibroblast growth factor 2 (FGF2). The cells were cultured at 37° C. in a 5% $CO_2$ incubator. The cell proliferation rates were compared (FIG. 2 and FIG. 3).

As shown in FIG. 2, the umbilical cord blood stem cells (PMS) isolated and cultured in Example 1 exhibited a faster proliferation rate compared to the umbilical cord blood stem cells (CTR) isolated and cultured in Comparative Example 1.

Furthermore, as observed in FIG. 3, the umbilical cord blood stem cells (CTR) isolated and cultured in Comparative Example 1 ceased to grow after the 7th passage, while the umbilical cord blood stem cells (PMS) isolated and cultured in Example 1 continued to proliferate even beyond the 8th passage. Therefore, the present invention enables the mass production of a greater number of stem cells.

Example 3. Comparison of Extracellular Matrix (ECM) Secretion Ability of Umbilical Cord Blood Stem Cells Umbilical cord blood stem cells isolated from Example 1 and Comparative Example 1 were cultured through passages. Umbilical cord blood stem cells at each passage were seeded at a density of $4\sim10\times10^3$ cells/cm$^2$. After 24 hours, the cells were washed with PBS and the culture medium was exchanged with serum-free media. The cells were then cultured for 2-7 days to obtain the umbilical cord blood stem cell culture supernatant.

The expression levels of fibronectin in the umbilical cord blood stem cell culture supernatant for each passage were analyzed using an ELISA kit (FIG. 4).

As shown in FIG. 4, the umbilical cord blood stem cells derived from Example 1, which maintained high expression levels of GDF-3, exhibited a higher content of fibronectin in the culture supernatant compared to the control group of umbilical cord blood stem cells derived from Comparative Example 1.

Therefore, the umbilical cord blood stem cells isolated from Example 1 not only demonstrated enhanced cell proliferation compared to the umbilical cord blood stem cells derived from Comparative Example 1 but also exhibited increased secretion of ECM components.

Example 4. Analysis of GDF-3 mRNA Expression at Each Passage

Umbilical cord blood stem cells isolated from Example 1 and Comparative Example 1 were cultured through passages. Umbilical cord blood stem cells at each passage were washed with PBS and dissociated with Trypsin EDTA. The dissociated cells were resuspended in an equal volume of culture medium containing twice the amount of Trypsin EDTA to deactivate it. The suspended cells were centrifuged to remove the supernatant. The cell pellet was resuspended in PBS, followed by another centrifugation to remove the supernatant. Total RNA was extracted using the PureLink™ RNA Mini Kit (Invitrogen), and the concentration was determined. cDNA synthesis was performed using the extracted total RNA.

Real-Time PCR was conducted using the synthesized umbilical cord blood stem cell cDNA and the primers listed in Table 2 to quantify the expression levels of GDF-3 at each passage. GAPDH, a housekeeping gene, was used as the loading control (FIG. 5).

TABLE 2

| | | |
|---|---|---|
| GAPDH | Forward | GACCTGCCGTCTAGAAAAAC |
| | Reverse | TTGAAGTCAGAGGAGACCAC |
| GDF-3 | Forward | AGACTTATGCTACGTAAAGGA |
| | Reverse | CTTTGATGGCAGACAGGTTAA |

As observed in the graph in FIG. 5, the higher expression of GDF-3 is attributed to the faster proliferation.

Furthermore, as shown in FIG. 5, umbilical cord blood stem cells isolated from Example 1 (PMS) exhibited significantly higher levels of GDF-3 expression compared to the control group (CTR) of umbilical cord blood stem cells isolated from Comparative Example 1. Interestingly, it was observed that the expression of GDF-3 gradually increased with each passage.

Example 5. Analysis of Human Dermal Fibroblast (HDF) Characteristics Treated with GDF-3

During the cultivation of Human Dermal Fibroblasts (HDF), the cell characteristics were analyzed through mRNA analysis comparing the group treated with GDF-3 to the untreated control group. As shown in FIG. 6, the experimental results revealed significantly higher expression of the GDF-3 gene in the GDF-3 treated group.

Example 6. The Effects of GDF-3 on HDF Growth

During the cultivation of Human Dermal Fibroblasts (HDF) in DMEM medium, GDF-3 was administered at concentrations ranging from 1 to 100 ng/ml at 48-hour intervals. As shown in FIG. 7, it was observed that HDF growth was increased in the GDF-3 treated group compared to the untreated group. The cells in the GDF-3 treated group exhibited a more elongated and compact shape, favorable for proliferation. Furthermore, even after prolonged cultivation for more than 96 hours, the cells continued to proliferate without any signs of growth stagnation or decline. This indicates that GDF-3 has a positive impact on sustained cell growth (FIG. 7).

Example 7. Gene Expression Analysis of Extracellular Matrix (ECM) Components in GDF-3-High Expressing HDF The gene expression of skin structural components such as Collagen and Fibronectin, which are involved in skin regeneration, was examined using the Real-Time PCR technique following GDF-3 treatment (FIG. 8).

As shown in FIG. 8, it was observed that high expression of GDF-3 in HDF led to an increased gene expression of ECM components. This indicates that sustained GDF-3 expression in HDF promotes the upregulation of ECM component genes.

The invention claimed is:

1. A method of producing GDF-3-expressing umbilical cord blood-derived mesenchymal stem cells (UCB-MSCs) through passages, with a cell doubling time of 24 hours or less, wherein the UCB-MSCs with a cell doubling time of 24 hours or less are selectively isolated and cultured from umbilical cord blood mononuclear cells to obtain the UCB-MSCs that express GDF-3 at high levels.

2. The method of producing the GDF-3-expressing UCB-MSCs according to claim 1, wherein the higher the proliferation rate of the selectively isolated and cultured UCB-MSCs, the higher the expression level of GDF-3 in these cells.

3. The method of producing the GDF-3-expressing UCB-MSCs according to claim 1, which is used to establish a cell bank for umbilical cord blood stem cells with high expression of GDF-3.

4. The method of producing the GDF-3-expressing UCB-MSCs according to claim 1, comprising the following steps:

(i) seeding the mononuclear cells isolated from umbilical cord blood onto a culture dish containing a medium supplemented with TGF-superfamily growth factors; and (ii) selectively isolating and culturing the mononuclear cells with a cell doubling time of 24 hours or less that attach to the culture dish and exhibit relatively rapid proliferation.

5. The method of producing the GDF-3-expressing UCB-MSCs according to claim 1, wherein the GDF-3-expressing UCB-MSCs are used for producing a culture medium containing GDF-3.

6. The method of producing the GDF-3-expressing UCB-MSCs according to claim 1, wherein the expression level of GDF-3 increases gradually as the passages progress in the GDF-3-expressing UCB-MSCs.

7. The method of producing the GDF-3-expressing UCB-MSCs according to claim 1, wherein the GDF-3-expressing UCB-MSCs from passage 5 or higher are used, to obtain umbilical cord blood stem cells, which express high levels of GDF-3.

8. The method of producing the GDF-3-expressing UCB-MSCs according to claim 1, wherein the GDF-3-expressing UCB-MSCs are expanded through successive passages, to secure a large quantity of umbilical cord blood stem cells.

9. The method of producing the GDF-3-expressing UCB-MSCs according to claim 1, wherein the GDF-3-expressing UCB-MSCs are expanded through successive passages, to obtain a large quantity of umbilical cord blood stem cells with superior extracellular matrix secretion capability.

* * * * *